US005587297A

United States Patent [19]
Jacobson et al.

[11] Patent Number: 5,587,297
[45] Date of Patent: Dec. 24, 1996

[54] METHOD FOR IDENTIFICATION OF DISEASE-SPECIFIC SURFACE COMPONENTS OF VASCULAR ENDOTHELIAL CELLS

[75] Inventors: Bruce S. Jacobson, Amherst; Jan E. Schnitzer, Boston, both of Mass.

[73] Assignee: The Regents of the University of California, Oakland, Calif.

[21] Appl. No.: 185,433

[22] Filed: Jan. 24, 1994

Related U.S. Application Data

[63] Continuation-in-part of Ser. No. 928,912, Aug. 11, 1992, Pat. No. 5,281,700.

[51] Int. Cl.⁶ ............................ C12Q 1/02; G01N 33/48; C07K 1/18; C07K 1/30
[52] U.S. Cl. ...................... 435/29; 435/4; 435/34; 436/63; 436/64; 436/161; 436/173; 436/174; 436/177; 436/178; 436/813; 530/350; 530/395; 530/416; 530/418
[58] Field of Search ...................... 530/412, 415, 530/416, 427, 350, 395, 835, 837, 839, 841, 846, 849, 854, 418; 554/8, 19, 175, 191; 558/146; 435/4, 34, 29; 436/63, 64, 161, 162, 173, 174, 177, 178, 813

[56] References Cited

U.S. PATENT DOCUMENTS

| | | | |
|---|---|---|---|
| 3,007,878 | 11/1961 | Alexander et al. | 252/313.2 |
| 4,925,922 | 5/1990 | Byers et al. | 530/391 |
| 5,059,523 | 10/1991 | Rettig et al. | 435/7.23 |
| 5,169,774 | 12/1992 | Frankel et al. | 530/388.85 |
| 5,227,307 | 7/1993 | Bar-Or et al. | 436/63 |
| 5,281,700 | 1/1994 | Schnitzer et al. | 530/412 |

OTHER PUBLICATIONS

Burrow et al., *Canc. Res.* 52: 5954–62, 1992.
Chaney and Jacobson, *J. Biol. Chem.* 258: 10062, 1983.
Clark and West, *Electrophoresis* 12: 590, 1991.
Gerritsen et al., *Adv. Cell Culture* 6: 35–67, 1988.
Gougas et al. *J. Biol. Chem.* 265: 8361–4, 1990.
Kumar et al., in *Angiogenesis in Health & Disease* 227: 63–78, 1992, Plenum Press NATO, Asi Series.
Mizrachi et al., *Cell & Tissue Res.* 256: 365–72, 1989.
Murray et al., *Radiother. Oncol.* 16: 221–34, 1989.
Ogawa et al., *Proc. Natl. Acad. Sci. USA.* 88: 9897–9901, 1991.
Patton, *Biochim & Biophys Acta* 816: 83–92, 1985.
Patton et al., *J. Cell Physiol.* 134: 37–46, 1988.
Rettig et al., *Proc. Natl. Acad. Sci., USA.* 89: 10832–6, 1992.
Sambuy et al., *Proc. Natl. Acad. Sci. USA.* 85: 1529–33, 1988.
Schnitzer, *Am. J. Physiol.* 262: H246–H254, 1992.
Schrappe et al., *Canc. Res.* 51: 4986–93, 1991.
Stolz et al., *In vitro Cell Dev. Biol.* 27A: 169–182, 1991.
Wang et al., *Int'l J. Can.* 54: 363–70, 1993.
Weidner et al., *NEJM* 324: 1–7, 1992.
Noguchi et al. "Identification & Partial Purification of A Novel Tumor Derived Protein That Induces Tissue Factor On Cultured Human EndoThelial Cells" Biochem Biophys. Res Comm 160 (1) 222–227 1989.

*Primary Examiner*—Mindy Fleisher
*Assistant Examiner*—Nancy J. Degen
*Attorney, Agent, or Firm*—Brown, Martin, Haller & McClain

[57] ABSTRACT

The present invention provides methods for identifying molecular components (e.g. proteins and/or lipids) that are characteristic of vascular endothelia associated with a particular disease and are not also present in (i) normal (non-disease associated) vascular endothelia or (ii) non-disease associated vascular endothelia subjected to altered conditions that accompany the disease but are not unique to the disease. The methods include isolating plasma membrane fractions from disease-associated vascular endothelial cells, from normal (nondisease-associated) vascular endothelial cells and from nondisease-associated vascular endothelial cells subjected to at least one of the altered conditions; purifying and resolving molecular components from these membrane fractions; comparing the components resolved from each of the foregoing vascular endothelial cell sources and identifying components that are present in disease-associated endothelial cells and absent from the normal or otherwise conditioned endothelial cells. The resulting endothelial cell membrane components that are unique to the disease state can be used for diagnostic and/or therapeutic purposes.

16 Claims, No Drawings

METHOD FOR IDENTIFICATION OF DISEASE-SPECIFIC SURFACE COMPONENTS OF VASCULAR ENDOTHELIAL CELLS

STATEMENT OF GOVERNMENT SUPPORT

This invention was made with Government support under Grant Contracts Nos. HL 43278 and GM 29127 awarded by the National Institutes of Health. The Government has certain rights in this invention.

CROSS-REFERENCE TO RELATED APPLICATION

This application is a Continuation-in-Part of commonly assigned U.S. application Ser. No. 07/928,912, filed Aug. 11, 1992, now U.S. Pat. No. 5,281,700, issued on Jan. 25, 1994 (referred hereinafter as the "parent application").

FIELD OF THE INVENTION

This invention pertains to methods for identifying endothelial cell surface molecules, primarily proteins and lipids, that are characteristic of various disease states, and the use of such molecules for the diagnosis and treatment of disease.

BACKGROUND OF THE INVENTION

The vascular endothelium is critically important for human and mammalian physiology and pathology. The luminal plasma membrane of vascular endothelial cells, in particular, plays a major role in regulating permeability, coagulation/anti-coagulation processes, interactions with migrating cells in inflammatory processes, and metastasis of neoplastic cells. Furthermore, the luminal plasma membrane interacts with vasoactive substances and cytokines that both up-regulate cell adhesion molecules and control the plasminogen activator-inhibitor system. The membrane also interacts with plasma proteins, such as transferrin, albumin, and others, to internalize and selectively transcytose these substances.

In addition to the constitutive activities listed above, vascular endothelial cells have different morphologies and functions depending upon the type of tissue they serve. Some of these differences, which are reflected in their complement of cell surface proteins, appear to be established during embryogenesis and are maintained unless the tissue is altered during adult life. Alterations in surface proteins of endothelial cells from the same type of tissue also occur incident to tissue damage or pathology as in, for example, inflammation, ischemia, and neoplastic processes.

Solid tumors in particular are highly vascularized. Even though tumor-associated blood vessels are originally derived from normal blood vessels, their morphology differs significantly from that of normal tissue. The microvasculature of solid tumors is mainly composed of capillaries and some undifferentiated vessels lined by endothelial cells with relatively few adjacent pericytes or smooth muscle cells. By contrast, normal capillaries have ample pericytes, which are thought to reduce endothelial cell proliferation and induce capillary maturation. Tumor capillaries also differ from normal blood vessels in possessing less basement membrane, reduced vessel stability, and increased vessel permeability relative to normal capillaries. These gross differences in structure and function are reflected in plasma membrane proteins that are expressed in tumor-associated vascular endothelial cells and are absent from normal endothelia.

There is a need in the art for reagents that detect disease-specific components, e.g. components of tumor-associated vasculature, for use as diagnostic probes. Furthermore, the same components can be used as targets for therapeutic reagents that will destroy tumor-associated blood vessels and thereby starve the tumor of critical oxygen and nutrients. In addition, intravasation of cancer cells, which takes place on tumor blood vessels, can be blocked by the same means. Finally, vascular targets can be used to deliver various medicaments such as chemotoxins to the immediate environment of a tumor.

The possibility of targeting tumor-associated blood vessels in order to inhibit the growth of tumors has now been tested in a model system. Burrows et al., *Canc. Res.* 52:5954–5962, 1992. When neuroblastoma cells transfected with gamma interferon genes were injected subcutaneously into mice, the tumors that formed produced gamma interferon. The gamma interferon up-regulated cell surface MHC Class II antigens in the vascular endothelial cells within the tumor. When these mice were subsequently administered a hybrid immunotoxin that recognized MHC Class II antigens, the tumors in the animal model were markedly reduced in size, without apparent damage to other organs. The above-described results, however, do not indicate which endothelial cell surface proteins might be up-regulated during tumor development in a natural condition. Nor do they suggest a way for distinguishing endothelial surface antigens that are expressed in response to the tumor itself from endothelial surface antigens expressed in any rapidly proliferating endothelium.

A number of other researchers have expended considerable effort (using a variety of experimental techniques) in an attempt to identify tumor-specific endothelial antigens. Several groups have used monoclonal antibodies (MAbs) raised against different source cells to probe normal and tumor-associated endothelia. Murray et al., (*Radiother. Oncol.* 16:221–234, 1989) demonstrated that MAb MECA-20 stains tumor-associated endothelia, but also effectively stains the vasculature of normal tissue. Rettig et al. (*Proc. Natl. Acad. Sci. USA* 89:10832–10836, 1992), using MAb FB5, showed that the antigen, which they termed endosialin, is present in tumor-associated endothelium but absent from normal endothelium. Endosialin is, however, synthesized at high levels in cultured fibroblasts, which strongly suggests that it is a proliferation-associated protein, and therefore of limited use as a target of tumor-associated vasculature. Similarly, Schrappe et al. (*Canc. Res.* 51:4986–4993, 1991) reported that a chondroitin sulfate proteolglycan recognized by MAb 9.2.27 is present in cultures of tumor cells as well as in tumor-associated endothelia but this molecule is also present in proliferating endothelia. Finally, Wang, J. M. et al., *Int'l J. Canc.* 54:363–370, 1993) reported that MAb E-9 stained endothelia that were tumor-associated, embryonic, or regenerating, and therefore did not specifically bind to tumor-associated endothelia. It is currently believed that the E-9 antigen, and possibly other proteins detected by the MAb technique, are in fact endoglin, a previously isolated and cloned polypeptide expressed at various levels in all endothelial cells except those in bone marrow (Gougas, A. et al., *J. Biol. Chem.* 265:8361–8364, 1990).

Clarke and West (*Electrophoresis* 12:590, 1991) used radio-iodination to label the cell surface of cultured endothelial cells exposed to different proliferative and tumor-derived stimuli in an attempt to isolate tumor-associated proteins. The majority of the proteins induced by tumor-conditioned medium were also shown to be induced by proliferative stimuli, although in that paper, three tumor-specific protein species were said to have been detected. However, there has been no follow-up report of any particular truly tumor-specific antigens. Moreover, the radioiodination technique has inherent limitations: it can only detect a relatively small subset of cell surface proteins (those having accessible tyrosine residues). If radioiodination cannot be detected in a test sample, this may mean that the protein is absent or that the protein is not labelled. This is a particular impediment when searching for tumor-specific endothelial surface proteins, because they are likely to be bound to growth factors and extracellular matrix components and thus masked from radioiodination. In addition, radioiodination probes can penetrate between endothelial cells to label nonendothelial cell proteins. Consequently, a protein that is iodinated is not necessarily made by endothelial cells. Furthermore, because only a small percentage of any one protein would be labeled by iodine, the labeling probe cannot be used in isolating the protein.

There is also a need in the art for reagents that detect other pathological changes in the surface of vascular endothelial cells, such as those that result from hypoxia and/or ischemia. Hypoxia is defined herein as deprivation of tissues of physiological levels of oxygen. Ischemia is the condition in which tissues are deprived of blood supply. In the case of heart attacks, an initial failure of blood flow leads to endothelial surface changes. This in turn initiates an inflammatory response in which neutrophils and other blood components adhere to the luminal surface of the endothelium, further constricting blood flow and exacerbating tissue damage. Identification of the relevant hypoxia-specific endothelial surface proteins would thus provide targets for diagnostic and therapeutic reagents. Agala, S. et al., *Proc. Natl. Acad. Sci. (USA)* 88:9897–9901, 1991 used two-dimensional gel electrophoresis to identify sixty apparently hypoxia-induced endothelial proteins, but their work did not discriminate between internal and surface proteins.

A method for physically isolating plasma membrane fractions from slime mold cells employing the colloidal silica technique (which the parent application has modified and applied to tissue) is disclosed by Chaney and Jacobson (*J. Biol. Chem.* 258:10062, 1983). In these experiments, however, the technique was not used to compare plasma membrane protein profiles of cells exposed to different proliferative or disease-mimicking stimuli, nor to identify disease-specific endothelial membrane molecules. Moreover, as will be explained further below, the art was resistant to use of endothelial cells in culture because of phenotypic drift and the possibility for artifact.

SUMMARY OF THE INVENTION

The present invention provides methods for identifying molecular components (e.g. proteins and/or lipids) that are characteristic of vascular endothelia associated with a particular disease and are not also present in (i) normal (non-disease associated) vascular endothelia or (ii) non-disease associated vascular endothelia subjected to altered conditions that accompany the disease but are not unique to said disease. The methods comprise isolating plasma membrane fractions from disease-associated vascular endothelial cells, from normal (nondisease-associated) vascular endothelial cells and from nondisease-associated vascular endothelial cells subjected to at least one of said altered conditions; purifying and resolving molecular components from these membrane fractions; comparing the components resolved from each of the foregoing vascular endothelial cell sources and identifying components that are present in disease-associated endothelial cells and absent from the normal or otherwise conditioned endothelial cells.

The resulting endothelial cell membrane components that are unique to the disease state can be used for diagnostic and/or therapeutic purposes.

DETAILED DESCRIPTION OF THE INVENTION

All patent applications, patents and publications cited in this specification are hereby incorporated by reference in their entirety. In the case of inconsistencies, the present disclosure, including definitions, will prevail.

In the parent application (the entire disclosure of which is specifically incorporated by reference), we have described novel, reliable methods for separating endothelial cell membrane molecules from associated tissue, isolating such molecules, and identifying molecules that are characteristic of endothelia associated with the vasculature in various disease states, including tumor growth. We believed it was necessary to use tissue as the starting material because (a) endothelial cells in culture are known to be subject to phenotypic drift and (b) despite claims to the contrary, other researchers using different techniques from that of the parent application have failed to identify any endothelial membrane molecules that were truly associated with tumor growth (as opposed to molecules that are expressed in any rapidly proliferating endothelium including normal rapidly proliferating endothelium, such as that present in normal tissue growth or healing of wounds).

The present invention relates to a method for identifying cell-surface molecular components of vascular endothelial cells that are specific to vascular endothelia derived from different disease states. Briefly, the method involves culturing vascular endothelial cells in vitro under conditions that mimic normal and disease conditions in vivo. Plasma membranes are then purified from the cultures, and protein and/or lipid components of the membranes are isolated and resolved. Comparison of the protein and/or lipid profiles of the different membranes reveals components that are unique to each original culture condition and reflect the native tissue in vivo. The presence of the same components in diseased tissue can be used to confirm that the in vitro identified components are indeed markers for endothelia associated with disease.

It is an important aspect of the present invention that the plasma membrane (and preferably the apical surface of the plasma membrane) be isolated from the total endothelial cell components (and preferably also from other membrane material) in order to provide a sample to be analyzed that is substantially enriched in endothelial cell membrane components which are of interest (and, conversely, substantially depleted of endothelial cell components from other parts of the cell, which are not of interest). It is also important that the analytical technique employed be sensitive (in detecting small amounts of disease-specific endothelial surface components) and relatively unaffected by the structure and properties of the components to be detected (for example, effectiveness of the technique should not depend on the presence or availability in a component of a particular binding site because unless that site is both present and available the component will remain undetected).

It has been recognized that when endothelial cells are removed from their in situ locations in tissues and cultured in vitro, they are subject to phenotypic drift, i.e. they begin to lose some of the morphological features (and components) characteristic of their tissue or organ of origin. As a result, simply excising vascular endothelial cells from normal and diseased tissues and culturing them in vitro is not satisfactory, since adaptation to culture conditions causes repression of components that are expressed in disease-associated endothelia or in normal endothelia (and may also cause expression of components that are not normally present in either disease-associated or normal endothelia).

According to the present invention, this problem is overcome by:

(a) striving to re-create important features of the in situ environment of the endothelial cells with respect to soluble factors or other conditions that are thought to influence their phenotypes, (e.g. exposing normal endothelial cells in culture to tumor-conditioned media); and (b) using a single endothelial cell culture as a starting material (from which aliquots are exposed to different conditions that mimic altered environments), to insure that the unique components that are detected in a particular culture subjected to disease-mimicking conditions are specific to the defined disease-mimicking treatments to which that culture has been subjected and are not due to other variables.

Questions about the existence of truly disease-associated endothelial membrane components have now been resolved for the following reasons:

1. A sufficient number of tumor-associated endothelial proteins were identified in endothelial membranes isolated from tissue using the method of the parent application. Even if only a relatively small number are truly tumor-associated (and allowing for repression caused by phenotypic drift) the identification of such specific tumor-associated components from culture is highly likely; and 2. Comparison of endothelial membrane surface proteins isolated from different (not diseased) tissues revealed a number of proteins that were specific to each tissue. Stolz, D. B. et al., *In vitro Cell Dev. Biol.* 27A:169–182, 1991. This also increases the likelihood that disease-associated endothelial membrane surface proteins are expressed in response to the presence of environmental changes that are uniquely associated with the disease, in that the endothelial cells are highly likely to respond to the tumor as though it were a different tissue.

As an illustration, using tumor-associated vascular endothelia isolated from tissue, the present inventors repeatedly found at least 10 and up to in excess of 20 luminal endothelial membrane proteins in each instance that were expressed in association with a particular tumor and were not expressed in normal (nontumor-associated) vascular endothelia of the same type. In addition, in experiments employing endothelial membrane material from different types of (non-diseased) tissue, the present inventors found at least 2–5 proteins detected in endothelial tissue from each given organ that were not encountered in tissues from other organs (data not shown).

Disease states which engender the expression of unique disease-associated endothelial membrane components include malignancies (particularly solid tumors), coronary artery disease, and ischemic states (such as those incident to myocardial infarctions or stroke). Additional such disease states are expected to include (without limitation) neurological disorders (e.g. Parkinson's disease or Alzheimer's disease), diseases of bone metabolism (e.g. osteoporosis) immune disorders (e.g. rheumatoid arthritis), pancreatic disorders (e.g. Type 1 diabetes), asthma and inflammation.

Non-limiting examples of endothelial cells useful in practicing the present invention include human umbilical vein endothelial cells (HUVECs), human umbilical arterial endothelial cells (HURECs), and human dermal microvascular endothelial cells (HUMECs), all of which are commercially available from Cell Systems Corp. (Kirkland, WA). In addition, a variety of human immortalized endothelial cell lines are available from the American Type Culture Collection (ATCC). If a particular type of endothelial cell is not commercially or publicly available, cultures can be established as disclosed for example in Stolz et al., *In Vivo Cell Dev. Biol.* 27A:169–182, 1991; or Gerritsen, M. et al., *Adv. Cell Culture* 6:35–67, 1988 and Schnitzer, *Am. J. Physiol.* 262:H246–H254, 1992.

Isolation of plasma membranes from cultured vascular endothelial cells is accomplished by techniques known in the art, which include: mechanical or hypotonic lysis of cells, followed by equilibrium sedimentation; attachment of nitrocellulose filters to the free surface of adherent cells (preferably previously coated by silica as disclosed e.g. in Sambuy, Y. et al., *Proc. Natl. Acad. Sci. (USA)* 85:1529–1533, 1988) followed by shearing of the plasma membrane attached to the filter; and attachment of magnetic particles to the exterior of the cells (Patton, W. F., *Biochim. & Biophys. Acta* 816:83–92, 1985) followed by homogenization and magnetic separation of the resulting plasma-membrane-derived vesicles. A preferred method employs cationic colloidal silica particles, and is described in detail in the parent application. (See, also Chaney et al., *J. Biol. Chem.* 258:10062, 1983.) Briefly, the cell surface is coated with the silica particles, after which sodium polyacrylate is applied as a second coat. The result is to cross-link the silica particles and form a dense pellicle with attached membrane fragments that can be separated from other cellular components by velocity sedimentation. The objective is to abstract from the cells endothelial plasma membrane components (preferably those on the apical surface of the plasma membrane).

Protein and/or lipid components of the purified membranes are then isolated using well-known methods. The particular technique used for the initial extraction of protein free of lipid, and vice versa, will depend on the subsequent method to be used for resolving different protein or lipid species, as will be appreciated by those skilled in the art. For example, proteins may be directly solubilized in sodium dodecyl sulfate and urea prior to two-dimensional (2-D) gel electrophoresis and/or column chromatography. Lipids may be extracted in different organic solvents prior to another separation step, e.g., using thin-layer or gas chromatography or column chromatography (e.g. HPLC).

Non-limiting examples of analytical methods for resolving protein species include molecular sieve, ion-exchange, and hydrophobic chromatography; polyacrylamide gel electrophoresis, with or without a prior isoelectric focusing step; and affinity chromatography using materials such as antibodies, or lectins as immobilized specific ligands.

It will be recognized that the methods for comparison of protein and lipid profiles derived from different starting cultures will depend on the analytical methods that produce those profiles. For example, 2-D gel electrophoresis produces complex electropherograms that are best analyzed using commercially available computer imaging software (e.g., MICROSCAN 1000 Technology Resources, Inc., Nashville, Tenn.). In any case, the result is to identify particular species that are present in the profile derived from the experimental culture (e.g. the culture exposed to disease-mimicking conditions) and absent from the control culture(s).

In one embodiment, normal endothelial cells are exposed to soluble factors secreted from tumor cells (tumor-conditioned media) that have been shown to influence the morphology and function of tumor-associated vascular endothelia. This is accomplished by either of two methods: 1) including tumor-conditioned medium in the growth medium of these cultures, or 2) co-culturing tumor cells and endothelial cells so that the endothelial cells are contacted by factors secreted by the tumor cells directly into the shared culture medium. By choosing the provenance of the tumor cells (e.g. breast carcinoma, malignant melanoma, colorectal carcinoma, etc.) or of the tumor-conditioned media, a tumor-type specific reaction can be induced in the endothelial cell. Mizrachi, Y. et al., *Cell & Tissue Res.* 256:365–372, 1989.

Human and animal tumor cells are widely available. The following is a nonlimiting listing of various tumor cell lines which are publicly available (e.g. from ATCC Human Tumor Bank) and which could be used to induce (or to generate culture media that induce) endothelial cell cultures to express tumorassociated molecules on their membrane surface.

| CELL LINE I.D. | TYPE |
| --- | --- |
| HTB-19 | Breast carcinoma |
| HTB-11 | Neuroblastoma |
| HTB-37 | Colon adenocarcinoma |
| HTB-53 | Lung carcinoma |

In another specific embodiment, vascular endothelial cells in culture are exposed to hypoxic conditions, so as to mimic the early stages of ischemia, a pathological state in which tissues are deprived of blood flow. This is achieved by incubating cells in an environment of 0–3% oxygen for periods ranging from about one minute to about two hours. The cell surface components on such cells are then compared with those on cells exposed to a normally oxygenated environment i.e. comprising about 20% oxygen, such as air.

As stated above, previous attempts to identify endothelial cell surface components that are specific to tumor-associated vascular endothelial cells relied upon an immunological approach that detected proteins that were touted as tumor-specific proteins, such as the protein called endoglin. It was subsequently found that endoglin is not unique to tumor-associated vasculature but is instead associated with all endothelial cells that are rapidly proliferating and with most that are thought to be quiescent. Gougas, et al., *J. Biol. Chem.* 265:8361–8364, 1990; Kumar, S., et. al., in *Angiogenesis in Health & Disease* 227:63–78, 1992, Plenum Press NATO, Asi Series. The property of rapid proliferation is shared by vascular endothelial cells in growing tumors, and those present in tissues undergoing remodeling, wound healing, or repair of other types of damage. While not wishing to be bound by theory, the findings with endoglin make it likely that a subset of plasma membrane components exists that is commonly expressed in all rapidly proliferating vascular endothelial cells. Such components are beyond the scope of the present invention and the methods claimed herein are specifically designed to exclude them from identification as tumor-specific endothelial membrane proteins. The present invention teaches instead how to distinguish endothelial cell-surface components that are induced by close association of endothelium with a tumor from those expressed in response to proliferation stimuli.

The present invention accomplishes this by employing one or more additional control cultures comprising endothelial cells derived from the same source and exposing them to conditions under which the cells proliferate rapidly (e.g., growing the cells in a pre-confluent state). The term "rapidly proliferating" is used to describe cells which double in number in a time period of 24–48 hours. This is in contrast to quiescent cells that do not double in number for a period of time of at least about 1 week.

The number of control cultures that can be used in the effort to exclude plasma membrane components expressed by conditions incident to but not unique to a disease state may vary depending on the disease state being studied. For example, when studying ischemic states it is preferable to analyze four different cultures: (i) hypoxic rapidly proliferating cells; (ii) hypoxic quiescent cells; (iii) rapidly proliferating cells exposed to normal oxygen levels; and (iv) quiescent cells exposed to normal oxygen levels. It is understood that a culture of rapidly proliferating cells is not a required part of an experiment unless the disease state induces rapid proliferation in the associated endothelium.

The length of time during which the cultured endothelial cells are exposed to the disease-mimicking (or proliferation-mimicking) conditions will vary with the particular stimulus. It will be recognized that a given stimulus may require a defined time period to exert its effect, which can be ascertained by routine experimentation using the methods of the present invention. For example, induction of a tumor-associated phenotype by co-culture of vascular endothelial cells with tumor cells may require several days longer than is required when previously tumor-conditioned medium is added to a culture containing only vascular endothelial cells (in which case incubation in the presence of tumor-conditioned media generally need last from about 2 hours to about 2 days). By contrast, inducing an ischemic phenotype in vitro is expected to occur on a time-scale of minutes to hours.

The association of a given protein or lipid component of the vascular endothelial plasma membrane with a particular disease state, as determined by the above-described methods, can be independently confirmed using in vivo-derived tissue. For example, specific (e.g. monoclonal) antibodies raised to a tumor-associated vascular component can be used to detect that component in tissue sections of a vascularized tumor, with non-tumor vascularized tissue used as a negative control. Alternatively, protein microsequencing using a protein spot excised from a 2-D gel will determine a short amino acid sequence from which synthetic degenerate oligonucleotides encoding that sequence can be derived. Such oligonucleotides can then be used to probe messenger RNA isolated from tumor and non-tumor associated endothelial tissue, or to generate larger probes for in situ hybridization to confirm the expression (or increased expression) of the protein in tumor-associated endothelium. Also, the technique of the parent application can be used to confirm whether a putative disease-associated marker identified in vitro is also observed in vivo, and use of this technique for confirmation is preferred.

The present inventors envision that antibody production, protein microsequencing, and oligonucleotide synthesis will enable the cloning of cDNA's encoding the disease-specific endothelial cell surface proteins. An endothelial cell cDNA expression library such as that cited in Gougos et al., (*J. Biol. Chem.* 265:8361–8364, 1990) can be screened with the specific antibodies or oligonucleotide profiles to identify the cognate cDNA clones. Extraction and sequencing of the phage or plasmid DNA present in the bacterial colonies will identify open reading frames corresponding to the amino acid sequence of a disease-specific endothelial surface protein. Comparison of the sequences with publicly available protein databases will provide added useful information on the structure and function of these disease-related proteins.

Protein or lipid components identified by the methods of the present invention can be advantageously used in the design of therapeutic and diagnostic reagents. Once an appropriate cell surface component has been identified, bifunctional reagents will be designed that will (1) bind specifically to the target molecule and (2) carry cytotoxic or other pharmacologically active agents. For example, antibodies specific to tumor-associated vascular antigens can be used to construct hybrid immunotoxins or other deleterious agents that will be targeted to the disease-associated vascular endothelium. The result will be to destroy the blood vessels that supply the tumor and thus inhibit tumor growth and metastasis. If the tumor-associated antigen is a receptor, its natural and synthetic specific ligands including agonists and antagonists, may be coupled to the bioactive agent. The specific ligands may be identified using combinatorial peptide libraries that are commercially available from e.g. Houghton Pharmaceuticals (La Jolla, Calif.). Conversely, a receptor protein (or active fragments thereof) that recognizes a disease-specific component on the endothelial surface can be coupled to a bioactive agent. Bioactive agents include without limitation toxins, chemotoxins, microspheres, coagulants, and complement factors. Toxins include without limitation ricin A chain, cholera toxins, and bacterial and viral toxins. Chemotoxins include without limitation methotrexate, hormones, 5-fluorouracil, and doxotubicin and its derivatives. Coagulants and microspheres can also be used to occlude the target capillaries, while complement factors can be used to directly lyse the target endothelial cells.

The components of the present invention can also be used to deliver to the vicinity of a tumor deleterious agents aimed at the tumor itself. As stated in the parent application, this approach obviates previous difficulties that have been encountered in directly targeting immunotoxins to the tumor cells themselves, e.g. the difficulty in gaining access to the tumor due to high interstitial pressure in the tumor, tight junctional complexes between tumor cells, and fibrous tumor stroma.

While the foregoing therapeutic approach can be customized, in that endothelial cells may be isolated and cultured from a particular individual from tumor and nontumor sites, and used to isolate tumor-specific components which would then become targets of therapy, a more practical approach is to identify and catalog tumor-specific antigens for various types of (preferably human) cancer and, if desirable, to use tissue from the patient to confirm their presence and level of expression. Such confirmation could be accomplished in ways known in the art, e.g., by biopsy including excision of tumor-associated vasculature and application of the methods described above for confirmation of the existence in vivo of a disease-specific protein or lipid.

The present invention also encompasses diagnostic reagents comprising or derived from disease-specific protein and lipid components. For example, the inventors envision that expression of unique endothelial cell surface molecules in response to an adjacent tumor will correlate with the presence of a malignancy and may correlate with the ability of that tumor to grow and/or metastasize. In the latter case, antibody or polynucleotide probes can be applied to biopsy tissue to quantify the expression of marker molecules and thus predict the course of disease and/or determine appropriate therapeutic strategies, or assess their effectiveness.

In the specific case of breast carcinomas, the extent of vascularization can be used as a prognostic indicator in the early stages of the disease. Weidner, M. et al., NEJM 324:1–7, 1992. The identification of endothelial membrane markers associated with such vascularization will improve the diagnostic ability of this technique. A similar strategy can be used for other solid tumors which induce substantial vascularization in their vicinity.

Ischemia-specific endothelial surface components identified by the methods of the present invention can also be used in the design and production of therapeutic and diagnostic reagents. Antibodies or other molecules (such as specific ligands or receptors or fragments thereof including the binding site) specific for such components can serve as delivery systems to target beneficial drugs to the damaged endothelium and to the ischemic tissue underlying it. This can be accomplished using the strategies described above with respect to tumor-associated endothelium. For example, since one manifestation of the ischemic state is increased blood coagulation, anticoagulant drugs can be targeted to the ischemic area to create an environment less favorable to coagulation. Furthermore, growth factors and antioxidants can be targeted to the relevant endothelial cells to repair or contain the ischemia-caused damage.

Diagnostic reagents that can detect and quantify ischemic damage are particularly important in treatment strategies, since tissue destruction after mild-to-moderate heart attacks often progresses for several days after the initial infarct. This exacerbation is due to a secondary inflammatory response mediated by exposure of the affected endothelial surface to the general blood circulation. Antibodies specific to hypoxic endothelial surface proteins can be coupled to thallium and administered intravenously after a heart attack. They are predicted to localize at the site of ischemic damage, and can be visualized using Positron Emission Tomography (PET scan). In this manner the severity of the tissue damage can be measured and used to predict later scarring and weakening of the heart wall.

The following examples are intended to further illustrate the invention without limiting its scope.

EXAMPLE 1

INDUCTION OF A TUMOR-ASSOCIATED PHENOTYPE IN CULTURES OF VASCULAR ENDOTHELIAL CELLS

Human umbilical cord endothelial cells (HUVECs) are grown in culture as previously described (Patton et al., J. Cell. Physiol. 134:37–46, 1988). HUVECs are purchased from Cell Systems Corp. (Kirkland, Wash.). Cell Systems pools endothelial cells from over 100 individual umbilical veins and tests them for the presence of HIV. Cultures are maintained in M-199 medium, supplemented with 20% FBS 100 units/ml penicillin, 100 µg/ml streptomycin and 2.5 µg/ml fungizone ill a 37° C. incubator with 5% $CO_2$. Cultures are inoculated into several sub-cultures for the following treatments prior to isolation of plasma membranes:

1) Rapidly proliferating: Cells are maintained for 1–2 days after a 1:2 to 1:3 subculture from a confluent monolayer.

2) Quiescent (i.e. non-proliferating): Cells are maintained in culture for 3–6 days post-confluence.

3) Tumor-associated (passive): The culture medium will be supplemented with tumor-conditioned medium. This medium is prepared by growing tumor cells for 1–4 days, removing and filtering the medium, and using it to supplement the endothelial cell growth by medium to a final concentration of 10% volume.

4) Tumor-associated (active): HUVECs are grown as monolayers on the surface of gelatin-coated multiwell tissue culture plates. Tumor cells are grown in multiple layers on membrane-bound tissue culture inserts (Fisher Scientific, Medford, Mass.). The membranes have a pore diameter of 0.45 microns, which allows the passage of large molecules but not whole cells. The multiwell plate with the inserts is placed on a rotary shaker and rotated for 3 min once an hour to insure mixing of any factors secreted by the tumor cells with the medium in contact with the endothelial cells. (It should be noted that it is not necessary to use both cultures (3) and (4) but it is preferred.)

EXAMPLE 2

INDUCTION OF AN HYPOXIA-ASSOCIATED PHENOTYPE IN CULTURES OF VASCULAR ENDOTHELIAL CELLS

Human umbilical cord endothelial cells are grown and subcultured as described in Example 1. Parallel cultures of rapidly proliferating and quiescent cells (as described in Example 1) are subjected to the following treatments:

1) Normal growth medium equilibrated with 20% oxygen; and
2) Identical growth medium equilibrated with air containing 0–3% oxygen.

Cells are exposed to these treatments for different times, ranging from about one minute to about two hours, prior to isolation of plasma membranes.

EXAMPLE 3

ISOLATION OF PLASMA MEMBRANE FRACTIONS FROM CULTURED VASCULAR ENDOTHELIAL CELLS USING CATIONIC COLLOIDAL SILICA

The isolation of plasma membranes from endothelial cells grown in culture is based on increasing the density of the membrane by coating it with cationic colloidal silica, which has a density of 2.55 g/cm$^3$.

Prior to coating, the cells may be removed from the culture dish by sequential treatment with collagenase and EDTA, which does not alter the protein composition of the surface. Alternatively, the cells may be retained as an adherent monolayer. In either case, the cells are washed (for 1–2 min.) in MES-buffered saline (MBS; 125 mM NaCl and 20 mM 2-(N-morpholino)ethanesulfonic acid (MES), pH 6) and chilled to 10°–15° C.

In the second step, the surface of the cells is coated (for 1–2 min.) with positively charged colloidal silica (1.5% by weight in MBS) (Alexander, G. V. and Bolt, G. H., U.S. Pat. No. 3,007,878). After several washes with MBS without silica to remove unabsorbed silica, the silica-coated cells are then overcoated with negatively charged sodium polyacrylate (1% in MBS). (Aldrich Chem. Co., St. Louis, Mo.) This serves to neutralize any exposed positively charged regions on the silica, forming a stable pellicle of silica crosslinked with polyacrylate. The washing and coating steps are for 1–2 minutes each and are performed at 4° C.

The washed, coated, cross-linked cells are then suspended in a solution containing 0.25M sucrose in 25 mM HEPES (N-(2-hydroexythyl)piperazine-N'2-ethanesulfonic acid) pH 7.2 and supplemented with the following protease inhibitors: leupeptin, pepstatin A, and trans-epoxysuccinyl-L-leucylamido(4-guanidino)butane (10 µg/ml each); 1 mM 0-phenanthroline; and 2 mM phenylmethylsulfonyl fluoride. The cells are homogenized using a Teflon pestle-glass homogenizer. The pestle is rotated at about 15–100 rpm and simultaneously also moved vertically in the homogenizer. The homogenate is then diluted with an equal volume of 1.02 g/ml Nycodenz (Sigma Chem. Co., St. Louis, Mo.) and layered over 1.37 g/ml Nycodenz. Centrifugation at 60,000×g for 20 min in a Beckman SW60ti rotor results in the appearance of a glass pellet at the bottom of the tube, which is recovered after aspiration of the solution. The pellet is then resuspended in sucrose/HEPES solution, mixed with an equal volume of 1.02 g/ml Nycodenz and recentrifuged through a layer of 1.37 g/ml Nycodenz. The resulting pellet contains silica-coated plasma membrane fragments with few contaminating structures or membranes.

EXAMPLE 4

RESOLUTION OF VASCULAR ENDOTHELIAL PLASMA MEMBRANE PROTEINS SPECIFIC TO ENDOTHELIAL CELL CULTURES SUBJECTED TO DIFFERENT CONDITIONS

The membrane proteins obtained in the pellet of Example 3 were released and solubilized from the silica/polyanion pellicle by sodium dodecyl sulfate. The procedures for solubilization, the gel compositions and electrophoresis conditions for isoelectric focusing and high-resolution SDS-PAGE, were as described in Stolz & Jacobson, supra, p. 172, 1991 as well as in the parent application.

The results indicate that each culture has a subset of unique plasma membrane proteins.

EXAMPLE 5

DETERMINING PARTIAL AMINO ACID SEQUENCES OF TUMOR-ASSOCIATED ENDOTHELIAL MARKERS AND PRODUCTION OF NUCLEIC ACID PROBES DERIVED THEREFROM

Proteins isolated as spots on 2-D gels are transferred to nylon membranes and then directly subjected to automated N-terminal microsequencing, using e.g. Applied Biosystems 120A apparatus Analyzer from Appl. Biosystems, Foster City, Calif. If the protein has been resolved by another technique (e.g. column chromatography), the fractions containing the protein of interest are pooled and the protein is concentrated prior to microsequencing. If the amino terminus of a particular polypeptide is blocked, and therefore refractory to Edman degradation, the protein sample is subjected to a mild proteolytic digestion (with, e.g. trypsin, streptolysin, and the like), and the resulting peptides are purified preferably by reverse-phase high-performance liquid chromatography and microsequenced.

Sequences comprising 10–15 amino acid residues are easily obtainable by currently available microsequencing systems and are sufficient for the present purpose. Once a sequence has been ascertained, a mixture of degenerate oligonucleotides encoding the complementary (antisense) sequence is synthesized in a commercially available oligonucleotide synthesizer.

EXAMPLE 6

CONFIRMATION OF UNIQUENESS OF TUMOR-ASSOCIATED MARKER PROTEINS IDENTIFIED IN CULTURE

Once tumor-associated endothelial marker proteins have been identified in cultured cells, their presence in tumor-associated endothelium in vivo is tested using preferably two independent approaches, as described below:

1) Immunological: Polyclonal or monoclonal antibodies are raised to individual protein species. The purified proteins may be derived from a spot on a 2-D gel. In this case, the gel area containing the protein of interest may be excised directly, pulverized, and used as an immunogen; alternately, the protein may be electrotransferred to a nitrocellulose or nylon membrane, which is then used as an immunizing matrix. If the protein has been resolved by another technique (e.g. column chromatography), the fractions containing the protein of interest are pooled and the protein is concentrated prior to immunization.

Both polyclonal and monoclonal antibody preparation and characterization are achieved using procedures that are standard in the art (see, e.g. Antibodies: A Laboratory Manual, Cold Spring Harbor, 1986). The antibody preparations are tested for high-affinity binding to the immunogen, and only antibodies showing association constants of $>10^7$ $M^{-1}$ are preferably used in subsequent steps.

Frozen sections of solid tumors and control tissues are prepared using standard techniques. The sections are then stained with the antibodies described above, followed by incubation with a secondary antibody conjugated to e.g. horseradish peroxidase and development of the peroxidase labelling using the diaminobenzidine reaction. Sections are then examined in the light microscope. Antibodies directed to authentic tumor-associated endothelial marker proteins that are present in sufficient abundance selectively stain tumor-associated vasculature, with little or no staining of normal vascular endothelial cells.

To ascertain whether a given protein is present on the apical or basolateral plasma membrane of the endothelial cells, ultra-thin frozen sections are prepared, stained as described above, and processed for electron microscopy.

2) Hybridization: The synthetic oligonucleotides containing partial complementary sequences corresponding to a subsequence of the protein of interest, prepared as described in Example 5, are used to detect and quantify the protein in tumor-associated vascular endothelium. Two different ways of accomplishing this are exemplified below:

a) Northern blot hybridization: Total RNA is prepared from a solid tumor, and from control tissues, using standard techniques such as hot phenol or guanidine isothiocyanate-based purification protocols. This RNA is then resolved on agarose gels, with or without prior purification of messenger RNA using oligo-dt cellulose chromatography. The RNA is then transferred to nitrocellulose, and the filters are probed with labelled antisense oligonucleotides.

b) In situ hybridization: For detection of protein expression in intact tissues, the antisense oligonucleotides are first used to produce longer polynucleotide probes by performing a primer extension reaction, with tissue-derived mRNA as a template. The resulting probes are used to stain tissue sections from solid tumors and control tissues that have been prepared for in situ hybridization by standard techniques.

In light of the above description, it will be apparent to those skilled in the art that the present invention is amenable to various additions, omissions and modifications all within the scope of the following claims:

What is claimed is:

1. A method for the identification of molecular components that are specific to tumor-associated vascular endothelium and are not also present in rapidly proliferating non-tumor-associated vascular endothelium, the method comprising the following steps:

(a) isolating plasma membrane fractions from (i) tumor-associated vascular endothelium, (ii) non-proliferating, non-tumor-associated vascular endothelium, and (iii) rapidly proliferating, non-tumor-associated vascular endothelium, which fractions are substantially enriched in endothelial cell membrane constituents containing said components and substantially depleted of non-membrane endothelial cell constituents;

(b) purifying said components from said membrane fractions;

(c) resolving individual components on the basis of differences in at least one of molecular mass, charge, and hydrophobicity to generate a components profile;

(d) comparing the profiles of plasma membrane fractions derived from (i)–(iii);

(e) identifying resolved molecular components present in (i) and absent from both (ii) and (iii).

2. The method of claim 1 wherein said components are selected from the group consisting of proteins and lipids of the plasma membrane surface of vascular endothelial cells.

3. The method of claim 1 wherein said vascular endothelium is derived from a tissue selected from the group consisting of umbilical, pulmonary, cardiac, cerebral, hepatic, and endocrinous tissue.

4. The method of claim 1 wherein said isolating step comprises contacting said vascular endothelium with an adherent first ionic material to form a coating, forming said coating into a pellicle adherent to a sheet of said endothelial membrane by contacting said coating with an oppositely charged second ionic material reactive with said first ionic material, homogenizing said endothelium, and separating said pellicle with said endothelial membrane sheet adhered thereto from other tissue elements.

5. The method of claim 4 wherein said first ionic material comprises colloidal silica and said second ionic material comprises acrylic polymer.

6. The method of claim 1 wherein said purifying step comprises extraction of said membrane fractions with at least one of detergent solutions and organic solvents.

7. The method of claim 1 wherein said vascular endothelium is grown in cell culture.

8. The method of claim 1 wherein said resolving step comprises an analytical method selected from the group consisting of molecular sieve, ion-exchange, hydrophobic chromatography, polyacrylamide gel electrophoresis, isoelectric focusing, mass spectrometry, gas chromatography, and thin-layer chromatography.

9. A method for inhibiting the growth of a tumor which comprises contacting tumor-associated vascular endothelium with an agent that is deleterious to vasculature and that binds specifically to at least one of the protein and lipid components that are specific to tumor-associated vascular endothelium and are not also present in rapidly proliferating non-tumor-associated vascular endothelium.

10. The method of claim 9 wherein said agent comprises a bifunctional reagent having a first moiety that binds specifically to said at least one of said protein and lipid components; and a second moiety comprising a pharmacologically active agent.

11. A method for the identification of molecular components that are specific to ischemic vascular endothelium and are not also present in non-ischemic vascular endothelium, which comprises the following steps:

(a) isolating plasma membrane fractions from (i) hypoxic vascular endothelium, (ii) non-hypoxic vascular endothelium, (iii) hypoxic rapidly proliferating vascular endothelium, and (iv) non-hypoxic rapidly proliferating endothelium, which fractions are substantially enriched in endothelial cell membrane constituents containing said components and substantially depleted of non-membrane endothelial cell constituents;

(b) purifying said components from said membrane fractions;

(c) resolving individual components on the basis of differences in at least one of molecular mass, charge, and hydrophobicity to generate components profiles for each of said endothelia (i) through (iv);

(d) comparing the profiles of plasma membrane fractions derived from (i) through (iv); and (e) identifying resolved proteins and lipids present in (i) and absent from (ii) through (iv).

12. The method of claim 11 wherein said isolating step comprises contacting said vascular endothelium with an adherent first ionic material to form a coating, forming said coating into a pellicle adherent to a sheet of said endothelial membrane by contacting said coating with an oppositely charged second ionic material reactive with said first ionic material, homogenizing said endothelium, and separating said pellicle with said endothelial membrane sheet adhered thereto from other tissue elements.

13. The method of claim 11 wherein said first ionic material comprises colloidal silica and said second ionic material comprises acrylic polymer.

14. The method of claim 11 wherein said purifying step comprises extraction of said membrane fractions with at least one of detergent solutions and organic solvents.

15. The method of claim 11 wherein said resolving step comprises an analytical method selected from the group consisting of molecular sieve, ion-exchange, hydrophobic chromatography, polyacrylamide gel electrophoresis, isoelectric focusing, mass spectrometry, gas chromatography, and thin-layer chromatography.

16. The method of claim 11 wherein said hypoxic and nonhypoxic vascular endothelia are grown in cell culture.

* * * * *